United States Patent
Park et al.

(10) Patent No.: US 9,434,998 B2
(45) Date of Patent: Sep. 6, 2016

(54) DNA CHIP FOR DIAGNOSIS OF GENITOURINARY INFECTIONS

(75) Inventors: Hyun Gyu Park, Daejeon (KR); Ye Lim Jung, Daejeon (KR); Won-Young Chung, Daejeon (KR); Ki Soo Park, Daejeon (KR); Cheulhee Jung, Daejeon (KR); Sung Chul Shin, Daejeon (KR); Dae-Yeon Cho, Sungnam-Si (KR); Sangjoon Hwang, Seoul (KR); Hyo Won Park, Seoul (KR)

(73) Assignees: Korea Advanced Institute of Science and Technology, Daejeon (KR); Labgenomics Co., Ltd., Seongnam-Si (KR)

( * ) Notice: Subject to any disclaimer, the term of this patent is extended or adjusted under 35 U.S.C. 154(b) by 22 days.

(21) Appl. No.: 14/361,678

(22) PCT Filed: Nov. 29, 2011

(86) PCT No.: PCT/KR2011/009150
§ 371 (c)(1),
(2), (4) Date: May 29, 2014

(87) PCT Pub. No.: WO2013/042824
PCT Pub. Date: Mar. 28, 2013

(65) Prior Publication Data
US 2014/0336082 A1 Nov. 13, 2014

(51) Int. Cl.
| C12Q 1/68 | (2006.01) |
| C12P 19/34 | (2006.01) |
| C07H 21/02 | (2006.01) |
| C07H 21/04 | (2006.01) |
| C12Q 1/70 | (2006.01) |

(52) U.S. Cl.
CPC ............ C12Q 1/689 (2013.01); C12Q 1/6883 (2013.01); C12Q 1/6895 (2013.01); C12Q 1/705 (2013.01); C12Q 1/6837 (2013.01); C12Q 2600/112 (2013.01); C12Q 2600/16 (2013.01)

(58) Field of Classification Search
CPC ............ C12Q 1/689; C12Q 2600/112; C12Q 1/6809; C12Q 1/6888; C12Q 1/70; C12Q 2600/16; G01N 2333/35
See application file for complete search history.

(56) References Cited

U.S. PATENT DOCUMENTS

2001/0053519 A1* 12/2001 Fodor ................. B01J 19/0046
435/6.11

FOREIGN PATENT DOCUMENTS

| JP | 2009-523442 A | 6/2009 |
| KR | 10-2004-0022705 A | 3/2004 |
| KR | 10-2004-0076201 A | 8/2004 |
| KR | 10-0619189 B1 | 8/2006 |
| KR | 10-2008-0024503 A | 3/2008 |
| KR | 10-0819634 B1 | 4/2008 |
| KR | 10-2010-0058919 A | 6/2010 |
| KR | 10-2011-0041829 A | 4/2011 |
| WO | 2007/083928 A1 | 7/2007 |

OTHER PUBLICATIONS

Chung W.-Y. et al. Biosensors and Bioelectronics 26 (2011) 4314-4319.*
Frenkl, "Sexually Transmitted Diseases," *Campbell-Walsh Urology*, pp. 371-385 (2007).
Lee, et al., "Rapid One Step Detection of Pathogenic Bacteria in Urine with Sexually Transmitted Disease (STD) and Prostatitis Patient by Multiplex PCR Assay (mPCR)," *Microbiol.*, vol. 45(5), pp. 453-459 (2007).
McNulty, et al., "Diagnosis of genital chlamydia in primary care: an explanation of reasons for variation in chlamydia testing," *Sex. Transm. Infec.*, vol. 80(207), pp. 207-211 (2004).
International Search Report and Written Opinion for PCT/KR2011/009150 mailed Oct. 23, 2012.

* cited by examiner

*Primary Examiner* — Stephen Kapushoc
(74) *Attorney, Agent, or Firm* — Kilpatrick Townsend & Stockton LLP

(57) ABSTRACT

A DNA chip for diagnosis of genitourinary infection, and in particular, a DNA chip for diagnosis of genitourinary infection on which oligonucleotide probes for detecting fourteen genitourinary infection pathogens are immobilized is provided. The DNA chip for diagnosis of genitourinary infections may accurately and rapidly analyze infections of fourteen genitourinary infections including multiple infections in various samples with high sensitivity, high specificity, and high reproducibility. Accordingly, the DNA chip may be used for diagnosis and treatment of genitourinary infections in primary health care institutions.

14 Claims, 8 Drawing Sheets

```
                              SEQUENCE LISTING

<160> NUMBER OF SEQ ID NOS: 66

<210> SEQ ID NO 1
<211> LENGTH: 44
<212> TYPE: DNA
<213> ORGANISM: Artificial Sequence
<220> FEATURE:
<223> OTHER INFORMATION: synthetic primer

<400> SEQUENCE: 1
ttttttttta ttacttaata gtcaaaactt tcaacaacgg atct                      44

<210> SEQ ID NO 2
<211> LENGTH: 44
<212> TYPE: DNA
<213> ORGANISM: Artificial Sequence
<220> FEATURE:
<223> OTHER INFORMATION: synthetic primer

<400> SEQUENCE: 2
ttttttttta ccccaccatt tttccggagc gagttacgaa gaca                      44

<210> SEQ ID NO 3
<211> LENGTH: 44
<212> TYPE: DNA
<213> ORGANISM: Artificial Sequence
<220> FEATURE:
<223> OTHER INFORMATION: synthetic primer

<400> SEQUENCE: 3 ttttttttg ggctttgatc cgaggatttc cgaatgggga gacc                       44

<210> SEQ ID NO 4
<211> LENGTH: 44
<212> TYPE: DNA
<213> ORGANISM: Artificial Sequence
<220> FEATURE:
<223> OTHER INFORMATION: synthetic primer

<400> SEQUENCE: 4 ttttttttt acgtgggtca ttggcgtggg gggttacagc gaca                       44

<210> SEQ ID NO 5
<211> LENGTH: 44
<212> TYPE: DNA
<213> ORGANISM: Artificial Sequence
<220> FEATURE:
<223> OTHER INFORMATION: synthetic primer

<400> SEQUENCE: 5 ttttttttg ttgagaaata ccttgatggt cagcaaaact ttgc                       44

<210> SEQ ID NO 6
<211> LENGTH: 44
<212> TYPE: DNA
<213> ORGANISM: Artificial Sequence
<220> FEATURE:
<223> OTHER INFORMATION: synthetic primer
```

```
<400> SEQUENCE: 6
tttttttttc gggtcgagag actgaacggc cacattggga ctga          44

<210> SEQ ID NO 7
<211> LENGTH: 44
<212> TYPE: DNA
<213> ORGANISM: Artificial Sequence
<220> FEATURE:
<223> OTHER INFORMATION: synthetic primer

<400> SEQUENCE: 7
tttttttttc gccaatatac ctaccaagct ccactgatag ggct          44

<210> SEQ ID NO 8
<211> LENGTH: 44
<212> TYPE: DNA
<213> ORGANISM: Artificial Sequence
<220> FEATURE:
<223> OTHER INFORMATION: synthetic primer

<400> SEQUENCE: 8
ttttttttta tcctaaaaaa ggtgtagaga aatatggtcc tgaa          44

<210> SEQ ID NO 9
<211> LENGTH: 44
<212> TYPE: DNA
<213> ORGANISM: Artificial Sequence
<220> FEATURE:
<223> OTHER INFORMATION: synthetic primer

<400> SEQUENCE: 9
tttttttttt tatggacgtc gtttcgatat tccatcaggt actg          44

<210> SEQ ID NO 10
<211> LENGTH: 44
<212> TYPE: DNA
<213> ORGANISM: Artificial Sequence
<220> FEATURE:
<223> OTHER INFORMATION: synthetic primer

<400> SEQUENCE: 10
tttttttttt attatgttag atggaagtgg cttaagtcgc tgtg          44

<210> SEQ ID NO 11
<211> LENGTH: 44
<212> TYPE: DNA
<213> ORGANISM: Artificial Sequence
<220> FEATURE:
<223> OTHER INFORMATION: synthetic primer

<400> SEQUENCE: 11
tttttttttg cttccgtaca ctcaagctca caacaccaac atac          44

<210> SEQ ID NO 12
<211> LENGTH: 44
<212> TYPE: DNA
<213> ORGANISM: Artificial Sequence
<220> FEATURE:
<223> OTHER INFORMATION: synthetic primer

<400> SEQUENCE: 12
ttttttttta tctggtggac tactcgccgg tcagcgaaaa acac          44
```

```
<210> SEQ ID NO 13
<211> LENGTH: 44
<212> TYPE: DNA
<213> ORGANISM: Artificial Sequence
<220> FEATURE:
<223> OTHER INFORMATION: synthetic primer

<400> SEQUENCE: 13
tttttttttg tcgccgggca ccaccacgcc gtattggtat tcgt            44

<210> SEQ ID NO 14
<211> LENGTH: 44
<212> TYPE: DNA
<213> ORGANISM: Artificial Sequence
<220> FEATURE:
<223> OTHER INFORMATION: synthetic primer

<400> SEQUENCE: 14
tttttttttg taaagttaat acctttgctc attgacgtta cccg            44

<210> SEQ ID NO 15
<211> LENGTH: 44
<212> TYPE: DNA
<213> ORGANISM: Artificial Sequence
<220> FEATURE:
<223> OTHER INFORMATION: synthetic primer

<400> SEQUENCE: 15
tttttttttc tttgttccct aagtccaact actaaactgg ggga            44

<210> SEQ ID NO 16
<211> LENGTH: 37
<212> TYPE: DNA
<213> ORGANISM: Artificial Sequence
<220> FEATURE:
<223> OTHER INFORMATION: synthetic primer

<400> SEQUENCE: 16
tttttttttt tttttcacg gttatcgctg aactcgg                     37

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
ccacaagtac cattcgtgcc                                       20

<210> SEQ ID NO 18
<211> LENGTH: 20
<212> TYPE: DNA
<213> ORGANISM: Artificial Sequence
<220> FEATURE:
<223> OTHER INFORMATION: synthetic primer

<400> SEQUENCE: 18
ccaggcatgg tgttcaattc                                       20

<210> SEQ ID NO 19
<211> LENGTH: 25
<212> TYPE: DNA
<213> ORGANISM: Artificial Sequence
<220> FEATURE:
<223> OTHER INFORMATION: synthetic primer
```

```
<400> SEQUENCE: 19
tcattactga tttgcttaat tgcac                                         25

<210> SEQ ID NO 20
<211> LENGTH: 22
<212> TYPE: DNA
<213> ORGANISM: Artificial Sequence
<220> FEATURE:
<223> OTHER INFORMATION: synthetic primer

<400> SEQUENCE: 20
aacgtccacc acgtatatct tc                                            22

<210> SEQ ID NO 21
<211> LENGTH: 22
<212> TYPE: DNA
<213> ORGANISM: Artificial Sequence
<220> FEATURE:
<223> OTHER INFORMATION: synthetic primer

<400> SEQUENCE: 21
caatggctaa tgccggatac gc                                            22

<210> SEQ ID NO 22
<211> LENGTH: 19
<212> TYPE: DNA
<213> ORGANISM: Artificial Sequence
<220> FEATURE:
<223> OTHER INFORMATION: synthetic primer

<400> SEQUENCE: 22
ggtaccgtca gtctgcaat                                                19

<210> SEQ ID NO 23
<211> LENGTH: 20
<212> TYPE: DNA
<213> ORGANISM: Artificial Sequence
<220> FEATURE:
<223> OTHER INFORMATION: synthetic primer

<400> SEQUENCE: 23
tatcaatttc aaccggctcc                                               20

<210> SEQ ID NO 24
<211> LENGTH: 21
<212> TYPE: DNA
<213> ORGANISM: Artificial Sequence
<220> FEATURE:
<223> OTHER INFORMATION: synthetic primer

<400> SEQUENCE: 24
ccacaaaaac tgtggtgtac c                                             21

<210> SEQ ID NO 25
<211> LENGTH: 21
<212> TYPE: DNA
<213> ORGANISM: Artificial Sequence
<220> FEATURE:
<223> OTHER INFORMATION: synthetic primer

<400> SEQUENCE: 25
ctaggcgttt gtactccgtc a                                             21
```

```
<210> SEQ ID NO 26
<211> LENGTH: 20
<212> TYPE: DNA
<213> ORGANISM: Artificial Sequence
<220> FEATURE:
<223> OTHER INFORMATION: synthetic primer

<400> SEQUENCE: 26
tcctcagaag tttatgcact                                               20

<210> SEQ ID NO 27
<211> LENGTH: 20
<212> TYPE: DNA
<213> ORGANISM: Artificial Sequence
<220> FEATURE:
<223> OTHER INFORMATION: synthetic primer

<400> SEQUENCE: 27
caggctgcct atcagaaagt                                               20

<210> SEQ ID NO 28
<211> LENGTH: 20
<212> TYPE: DNA
<213> ORGANISM: Artificial Sequence
<220> FEATURE:
<223> OTHER INFORMATION: synthetic primer

<400> SEQUENCE: 28
gctcaaggcc cttcataata                                               20

<210> SEQ ID NO 29
<211> LENGTH: 19
<212> TYPE: DNA
<213> ORGANISM: Artificial Sequence
<220> FEATURE:
<223> OTHER INFORMATION: synthetic primer

<400> SEQUENCE: 29
tgggttaagg caatagcaa                                                19

<210> SEQ ID NO 30
<211> LENGTH: 21
<212> TYPE: DNA
<213> ORGANISM: Artificial Sequence
<220> FEATURE:
<223> OTHER INFORMATION: synthetic primer

<400> SEQUENCE: 30
tgtattttcc caaggtttga a                                             21

<210> SEQ ID NO 31
<211> LENGTH: 20
<212> TYPE: DNA
<213> ORGANISM: Artificial Sequence
<220> FEATURE:
<223> OTHER INFORMATION: synthetic primer

<400> SEQUENCE: 31
ataccgcata acgtcgcaag                                               20

<210> SEQ ID NO 32
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 32
ccaccggtat tcctccagat                                            20

<210> SEQ ID NO 33
<211> LENGTH: 20
<212> TYPE: DNA
<213> ORGANISM: Artificial Sequence
<220> FEATURE:
<223> OTHER INFORMATION: synthetic primer

<400> SEQUENCE: 33
ctcagcaaat gcatcacaaa                                            20

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
ccaagccttg acgaactaaa                                            20

<210> SEQ ID NO 35
<211> LENGTH: 25
<212> TYPE: DNA
<213> ORGANISM: Artificial Sequence
<220> FEATURE:
<223> OTHER INFORMATION: synthetic primer

<400> SEQUENCE: 35
agttgatgaa accttaaccc cttgg                                      25

<210> SEQ ID NO 36
<211> LENGTH: 25
<212> TYPE: DNA
<213> ORGANISM: Artificial Sequence
<220> FEATURE:
<223> OTHER INFORMATION: synthetic primer

<400> SEQUENCE: 36
ccgttgaggg gttttccatt tttgc                                      25

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
tgggacacat gccttcttgg                                            20

<210> SEQ ID NO 38
<211> LENGTH: 28
<212> TYPE: DNA
<213> ORGANISM: Artificial Sequence
<220> FEATURE:
<223> OTHER INFORMATION: synthetic primer

<400> SEQUENCE: 38
acccttagtc agactctgtt acttaccc                                   28
```

```
<210> SEQ ID NO 39
<211> LENGTH: 21
<212> TYPE: DNA
<213> ORGANISM: Artificial Sequence
<220> FEATURE:
<223> OTHER INFORMATION: synthetic primer

<400> SEQUENCE: 39
atcctcgctt taggaacaac t                                           21

<210> SEQ ID NO 40
<211> LENGTH: 19
<212> TYPE: DNA
<213> ORGANISM: Artificial Sequence
<220> FEATURE:
<223> OTHER INFORMATION: synthetic primer

<400> SEQUENCE: 40
ccaactgccc ccttatcta                                              19

<210> SEQ ID NO 41
<211> LENGTH: 25
<212> TYPE: DNA
<213> ORGANISM: Artificial Sequence
<220> FEATURE:
<223> OTHER INFORMATION: synthetic primer

<400> SEQUENCE: 41
cattgataac gaagctcttt acgat                                       25

<210> SEQ ID NO 42
<211> LENGTH: 24
<212> TYPE: DNA
<213> ORGANISM: Artificial Sequence
<220> FEATURE:
<223> OTHER INFORMATION: synthetic primer

<400> SEQUENCE: 42
gcatgttgtg ccggacataa ccat                                        24

<210> SEQ ID NO 43
<211> LENGTH: 23
<212> TYPE: DNA
<213> ORGANISM: Artificial Sequence
<220> FEATURE:
<223> OTHER INFORMATION: synthetic primer

<400> SEQUENCE: 43
tctccaaagg tttctgatac agt                                         23

<210> SEQ ID NO 44
<211> LENGTH: 21
<212> TYPE: DNA
<213> ORGANISM: Artificial Sequence
<220> FEATURE:
<223> OTHER INFORMATION: synthetic primer

<400> SEQUENCE: 44
gtgagctctg ggactgtaag a                                           21

<210> SEQ ID NO 45
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 45
gctacgcata cccgcgttgc                                               20

<210> SEQ ID NO 46
<211> LENGTH: 20
<212> TYPE: DNA
<213> ORGANISM: Artificial Sequence
<220> FEATURE:
<223> OTHER INFORMATION: synthetic primer

<400> SEQUENCE: 46
cgaagacctt cgagcagaca                                               20

<210> SEQ ID NO 47
<211> LENGTH: 20
<212> TYPE: DNA
<213> ORGANISM: Artificial Sequence
<220> FEATURE:
<223> OTHER INFORMATION: synthetic primer

<400> SEQUENCE: 47
caagttggat cacatttcca                                               20

<210> SEQ ID NO 48
<211> LENGTH: 20
<212> TYPE: DNA
<213> ORGANISM: Artificial Sequence
<220> FEATURE:
<223> OTHER INFORMATION: synthetic primer

<400> SEQUENCE: 48
gccgtttaca cctcaaactt                                               20

<210> SEQ ID NO 49
<211> LENGTH: 22
<212> TYPE: DNA
<213> ORGANISM: Artificial Sequence
<220> FEATURE:
<223> OTHER INFORMATION: synthetic primer

<400> SEQUENCE: 49
aagatccact atcgccagca gg                                            22

<210> SEQ ID NO 50
<211> LENGTH: 22
<212> TYPE: DNA
<213> ORGANISM: Artificial Sequence
<220> FEATURE:
<223> OTHER INFORMATION: synthetic primer

<400> SEQUENCE: 50
attcagttcc gtttcccagc gg                                            22

<210> SEQ ID NO 51
<211> LENGTH: 19
<212> TYPE: DNA
<213> ORGANISM: Artificial Sequence
<220> FEATURE:
<223> OTHER INFORMATION: synthetic primer

<400> SEQUENCE: 51
ggtttgttgt gaggagcca                                                19
```

```
<210> SEQ ID NO 52
<211> LENGTH: 20
<212> TYPE: DNA
<213> ORGANISM: Artificial Sequence
<220> FEATURE:
<223> OTHER INFORMATION: synthetic primer

<400> SEQUENCE: 52
cctggaaaat ctccttagcc                                               20

<210> SEQ ID NO 53
<211> LENGTH: 18
<212> TYPE: DNA
<213> ORGANISM: Artificial Sequence
<220> FEATURE:
<223> OTHER INFORMATION: synthetic primer

<400> SEQUENCE: 53
ccatgcacgt aaaacacg                                                 18

<210> SEQ ID NO 54
<211> LENGTH: 18
<212> TYPE: DNA
<213> ORGANISM: Artificial Sequence
<220> FEATURE:
<223> OTHER INFORMATION: synthetic primer

<400> SEQUENCE: 54
gtgtgccgtt tttcgagt                                                 18

<210> SEQ ID NO 55
<211> LENGTH: 28
<212> TYPE: DNA
<213> ORGANISM: Artificial Sequence
<220> FEATURE:
<223> OTHER INFORMATION: synthetic primer

<400> SEQUENCE: 55
gatatttttc cgtaacgtct ctaagtct                                      28

<210> SEQ ID NO 56
<211> LENGTH: 26
<212> TYPE: DNA
<213> ORGANISM: Artificial Sequence
<220> FEATURE:
<223> OTHER INFORMATION: synthetic primer

<400> SEQUENCE: 56
gtctctaagt ctgctttcgt ttgttg                                        26

<210> SEQ ID NO 57
<211> LENGTH: 25
<212> TYPE: DNA
<213> ORGANISM: Artificial Sequence
<220> FEATURE:
<223> OTHER INFORMATION: synthetic primer

<400> SEQUENCE: 57
ttttcttcgt cagttaaacc ttccc                                         25

<210> SEQ ID NO 58
<211> LENGTH: 25
<212> TYPE: DNA
<213> ORGANISM: Artificial Sequence
<220> FEATURE:
<223> OTHER INFORMATION: synthetic primer
```

```
<400> SEQUENCE: 58
gataggacat ggctctacaa cgaac                                          25

<210> SEQ ID NO 59
<211> LENGTH: 25
<212> TYPE: DNA
<213> ORGANISM: Artificial Sequence
<220> FEATURE:
<223> OTHER INFORMATION: synthetic primer

<400> SEQUENCE: 59
atttgcaata ggaaatgatt gcaga                                          25

<210> SEQ ID NO 60
<211> LENGTH: 23
<212> TYPE: DNA
<213> ORGANISM: Artificial Sequence
<220> FEATURE:
<223> OTHER INFORMATION: synthetic primer

<400> SEQUENCE: 60
ccattactga cgcttaggct tga                                            23

<210> SEQ ID NO 61
<211> LENGTH: 25
<212> TYPE: DNA
<213> ORGANISM: Artificial Sequence
<220> FEATURE:
<223> OTHER INFORMATION: synthetic primer

<400> SEQUENCE: 61
tgacaatggc ttaggtctaa ccaaa                                          25

<210> SEQ ID NO 62
<211> LENGTH: 22
<212> TYPE: DNA
<213> ORGANISM: Artificial Sequence
<220> FEATURE:
<223> OTHER INFORMATION: synthetic primer

<400> SEQUENCE: 62
gtgcaaatgt gatccaactt gg                                             22

<210> SEQ ID NO 63
<211> LENGTH: 21
<212> TYPE: DNA
<213> ORGANISM: Artificial Sequence
<220> FEATURE:
<223> OTHER INFORMATION: synthetic primer

<400> SEQUENCE: 63
gcaaaggcag tccttgacaa c                                              21

<210> SEQ ID NO 64
<211> LENGTH: 22
<212> TYPE: DNA
<213> ORGANISM: Artificial Sequence
<220> FEATURE:
<223> OTHER INFORMATION: synthetic primer

<400> SEQUENCE: 64
aggctaaacc gagtacgtgt ga                                             22
```

```
<210> SEQ ID NO 65
<211> LENGTH: 19
<212> TYPE: DNA
<213> ORGANISM: Artificial Sequence
<220> FEATURE:
<223> OTHER INFORMATION: synthetic primer

<400> SEQUENCE: 65
agggcggcga ctttgacga                                                19

<210> SEQ ID NO 66
<211> LENGTH: 20
<212> TYPE: DNA
<213> ORGANISM: Artificial Sequence
<220> FEATURE:
<223> OTHER INFORMATION: synthetic primer

<400> SEQUENCE: 66
gggaggaagg cgcggagggg                                               20
```

DNA CHIP FOR DIAGNOSIS OF GENITOURINARY INFECTIONS

CROSS-REFERENCE TO RELATED APPLICATIONS

This application is the U.S. National Stage entry of PCT/KR2011/009150, filed Nov. 29, 2011, which is incorporated in its entirety herein.

REFERENCE TO SUBMISSION OF A SEQUENCE LISTING AS A TEXT FILE

The Sequence Listing written in file SEQTXT_96275-903981.txt, created on May 27, 2014, 9,410 bytes, machine format IBM-PC, MS-Windows operating system, is hereby incorporated by reference in its entirety for all purposes.

TECHNICAL FIELD

The present disclosure relates to a DNA chip for diagnosis of genitourinary infection, and more particularly, to a DNA chip for diagnosis of genitourinary infection on which oligonucleotide probes for detecting fourteen genitourinary infection pathogens are immobilized.

BACKGROUND ART

Conventionally, various methods, including microscopic tests via smearing and staining, bacterial culturing, antibiotics susceptibility tests, antigen-antibody tests, and immunological assays, are used to diagnose infectious diseases. However, such conventional diagnosis methods have limitations. Conventional methods are inconvenient or incompatible for a considerable number of specific bacteria species and time consuming, incur high costs and more manpower, and analyze a limited number of clinical specimens for a single assay. Furthermore, such methods are mostly only for one pathogen through a single test, and involve a non-automated result reading process, which hinders application for clinical use. They require living bacteria as target samples and thus viability of the bacteria should be kept till they are subject to the tests, which requires careful handling during the sample treatment and transportation, and consequently increases costs.

To address these drawbacks, in recent years, molecular genetic analyses have been pursued for infectious disease diagnosis, and have rapidly replaced the conventional methods. In particular, infection diagnosis by gene analysis using a DNA microarray or DNA chip for automated assay of multiple samples is drawing more attention, offers more advantages over the conventional infection diagnosis methods, and has been increasingly used as an auxiliary or alternative assay method for the conventional methods. Genetic diagnosis methods may accurately identify both main types and subtypes of target bacteria through DNA and RNA sequencing assays, and are also compatible with dead bacteria, thereby removing any need for difficult sample preparation and transportation processes. Genetic diagnosis methods involve target gene amplification through polymerase chain reaction (PCR), and thus may diagnose even a trace amount of a sample with high sensitivity. Genetic diagnosis methods also have high specificity and high reproducibility. Most genetic diagnosis methods rapidly provide accurate results in 24 hours, and require less manpower and less costs. In addition, genetic diagnosis using a DNA chip makes high throughput analysis of multiple samples possible.

A multiplex PCR method in which a plurality of polymerase chain reactions are conducted in a single test tube has been developed and widely used for diagnosis of bacterial infection (McNulty et al., *Sex. Transm. Infec.*, 80:207, 2004).

Genitourinary infectious disease is one of the most frequent bacterial infectious diseases, the second most next to respiratory infections, and about 78 to 330 million people are annually diagnosed as new patients with genitourinary infection (Lee et al., *J. Microbiol.*, 45:453, 2007). Some of these infectious diseases are sexual diseases that are legally designated as nationally notifiable communicable diseases (Class III) in Korea, which are likely to be intermittently epidemic, and thus require persistent incidence monitoring and preventive measures against them. In particular, sexual diseases are under sentinel surveillance. In the past, the diseases refer to specific diseases mediated by sex or sexual contact. However, since it was found that numerous diseases are mediated by sex or sexual contact, the generic term 'sexually transmitted diseases (STDs)' having a general meaning, has been used instead of the term 'sexual diseases' having a local meaning.

STD is a generic term referring to any of the diseases mediated by sex or sexual contact. Pathogenic bacteria causing STDs include *Neisseria gonorrhea*, which cause urethritis, prostatitis, or epididymitis in males and cervicitis, vaginitis, or pelvic inflammatory disease in females; *Chlamydia trachomatis; Ureaplasma urealyticum; Mycoplasma genitalium; Mycoplasma hominis; Trichomonas vaginalis; Herpes simplex virus; Treponema pallidum, Herpes simplex virus*, and *Haemophilus ducreyi*, which cause external genital ulcer; and human papilloma virus (HPV), which causes external genital warts, cervical cancer, anal cancer, or penile cancer. In addition to these bacteria causing STD, among those which do not cause STDs but cause STD-like symptoms such as vaginitis and thus require identification/detection are *Escherichia coli, Gardnerella vaginalis*, and the fungus *Candida albicans*.

It is reported that in the USA, annually, 15 hundred people are newly infected with STD, and 65 million or more people contract viral STDs. Despite such high morbidity rates, most genitourinary infections remain unrecognized and untreated because they are asymptomatic, but may advance to cause complications such as prostatitis, epididymitis, immune deficiencies, and cancers. In particular, efficacious treatment has not yet been found for most viral STDs. Thus, accurate diagnosis and prevention of STDs are the most important above all. Furthermore, it is also important to find and treat asymptomatic patients and prevent the spread of infections (Campbell-Walsh *Urology*, 2007).

In this regard, as a result of hard work to develop a method of simultaneously detecting multiple, highly-prevalent genitourinary infection-causing bacteria, the inventors of the present disclosure developed a DNA chip with immobilized oligonucleotide probes hybridizable with fourteen species of genitourinary infection pathogens which can accurately and rapidly analyze infections of the fourteen genitourinary infection pathogens, including multiple infections, in multiple samples, thereby completing the present disclosure.

DETAILED DESCRIPTION OF THE INVENTION

Technical Problem

The present invention provides a DNA chip for diagnosis of genitourinary infection.

Technical Solution

According to an aspect of the present disclosure, there is provided a DNA chip for diagnosis of genitourinary infection on which oligonucleotide probes having nucleotide sequences of SEQ ID Nos. 1 to 14 are immobilized.

In the DNA chip, the oligonucleotide probes having the nucleotide sequences of SEQ ID Nos. 1 to 14 may hybridize with DNA of genitourinary infection pathogens. The genitourinary infection pathogens may be selected from the group consisting of Escherichia coli (EC), Klebsiella pneumoniae (KP), Staphylococcus aureus (SA), Enterococcus faecalis (EF), Neisseria gonorrhea (NG), Chlamydia trachomatis (CT), Ureaplasma urealyticum (UU), Mycoplasma hominis (MH), Mycoplasma genitalium (MG), Trichomonas vaginalis (TV), Candida albicans (CA), Gardnerella vaginalis (GV), Herpes simplex virus-type 1 (HSV 1), and Herpes simplex virus-type 2 (HSV 2).

The DNA chip may further include an internal control and a position marker.

As used herein, the term 'internal control' refers to a probe immobilized on the DNA chip to verify whether an overall test process, including polymerase chain reaction (PCR) prior to hybridization onto the DNA chip, has been properly performed. In one embodiment of the present disclosure, the internal control may be an oligonucleotide probe having a nucleotide sequence of SEQ ID No. 15 that is hybridizable with a house keeping gene beta-globin detected in humans irrespective of bacterial infection.

As used herein, the term 'position marker' refers to a probe immobilized on the DNA chip to verify whether hybridization reaction has properly occurred. Prior to hybridization, a predetermined amount of a Cy3-dUTP-labeled anti-PM as an oligomer having a sequence complementary to the position marker may be added to a sample to identify whether hybridization and then, the positive signal thereof indicates that the hybridization has properly occurred.

In one embodiment of the present disclosure, the position marker may be an oligonucleotide probe having a nucleotide sequence of SEQ ID No. 16.

In one embodiment of the present disclosure, to develop new probes with improved specificities to genitourinary infection pathogens, a target site of each of the genitourinary infection pathogens is selected as follows: First, a probe sequence is selected from each pathogen specific 16S rRNA (18S rRNA for the eukaryote CA) and 23S rRNA genes that are generally used for phylogenetic analysis. When a suitable sequence is not available from these sequences, each pathogen-specific gene is searched and selected for probe sequences. The target sites selected as probes specific to respective genitourinary infection pathogens are shown in Table 1 along with GenBank Accession Nos. thereof.

TABLE 1

Target sites of genitourinary infection pathogens

| | Pathogen | Target site | GenBank Accession No. |
|---|---|---|---|
| 1 | Enterococcus faecalis (EF) | D-alanine ligase-related protein (ddl) gene | U00457.1 |
| 2 | Candida albicans (CA) | 18S rRNA gene | FJ159646 |
| 3 | Mycoplasma hominis (MH) | 16S rRNA gene | AJ002268.1 |
| 4 | Gardnerella vaginalis (GV) | 23S rRNA gene | CP002104.1 |
| 5 | Chlamydia trachomatis (CT) | cryptic plasmid pLGV440 | X06707.3 |
| 6 | Escherichia coli (EC) | 16S rRNA gene | AB609595.1 |
| 7 | Staphylococcus aureus (SA) | thermonuclease precursor (nuc) gene | EF529606.1 |
| 8 | Mycoplasma genitalium (MG) | MgPa operon gene | GU226196 |
| 9 | Herpes simplex virus-type 1 (HSV1) | RL1 gene | FJ593289.1 |
| 10 | Trichomonas vaginalis (TV) | beta-tubulin (btub1) gene | L05468.1 |
| 11 | Neisseria gonorrhea (NG) | cryptic plasmid pJD1 | M10316.1 |
| 12 | Ureaplasma urealyticum (UU) | serovar 13 urease complex component | AF085729.2 |
| 13 | Klebsiella pneumoniae (KP) | beta-lactamase SHV-103 (blaSHV-103) gene | EU032604 |
| 14 | Herpes simplex virus-type 2 (HSV2) | RL1 gene | Z86099.2 |

The nucleotide sequences of the target sites for respective pathogens and beta-globin gene, which were obtained using a BLAST engine (http://balst.ncbi.nlm.nih.gov) after selection of the target sites, were cross-checked against the nucleotide sequences of primers designed by using Primer 3 (Whitehead Institute)/MT Center for Genome Research). At least two candidate probes of 35 mer size that are able to minimize non-specific hybridization were designed for each pathogen by using OligoArray 2.0 (http://berry.engin.umich.edu/oligoarray). To verify the diagnostic capabilities of these candidate probes for the target pathogens, a screening test through hybridization using a DNA chip was conducted and optimal probes having the nucleotide sequences in Table 2 below were selected for the fourteen pathogens, an internal control, and a position marker. Each of these probes has a linker consisting of nine Ts at the 5' end, followed by a 35-mer probe sequence specific to a STD pathogen. The T-linker inserted as spacers may increase hybridization efficiency between the probe and PCR product.

In an embodiment of the present disclosure, a DNA chip may be manufactured by spotting and immobilizing each of the probes having nucleotide sequences of SEQ ID Nos. 1 to 16 as set forth in Table 2 below onto an aldehyde-coated glass substrate by using a microspotter equipped with SMP3 pins, putting on the glass substrate with the immobilized probes a reaction chamber serving as reaction wells and attaching a transparent film cover for preventing evaporation.

In an embodiment of the present disclosure, the DNA chip may include at least one section with a collection of probe spots, the collection of probe spots comprising three replicate spots per gene of the respective genitourinary infection pathogen, and the section comprises replicate spots for the internal control and the position marker in the middle thereof. In an embodiment of the present disclosure, the DNA chip may be a DNA chip in a form of a 4-plex array for simultaneous analysis of four samples that include four sections, each of which comprises a collection of the entire probe spots immobilized thereon. However, the number of sections in the DNA chip is not limited thereto and may vary depending on the number of samples to be analyzed at the same time.

nucleotide sequences of SEQ ID Nos. 17 and 18, a primer set for amplifying DNA of *Candida albicans* (CA) having nucleotide sequences of SEQ ID Nos. 19 and 20, a primer set for amplifying DNA of *Mycoplasma hominis* (MH) having nucleotide sequences of SEQ ID Nos. 21 and 22, a primer set for amplifying DNA of *Gardnerella vaginalis* (GV) having nucleotide sequences of SEQ ID Nos. 23 and 24, a primer set

TABLE 2

Nucleotide sequences of probes hybridizable with genes of genitourinary infection pathogens

| SEQ ID NO. | Probe Name | Start | Length | TM* | Sequence | Target pathogen |
|---|---|---|---|---|---|---|
| 1 | CA_1 | 214 | 9 + 35 | 70.1 | TTT TTT TTT ATT ACT TAA TAG TCA AAA CTT TCA ACA ACG GAT CT | *Candida albicans* (CA) |
| 2 | CT_1 | 112 | 9 + 35 | 67.2 | TTT TTT TTT ACC CCA CCA TTT TTC CGG AGC GAG TTA CGA AGA CA | *Chlamydia trachomatis* (CT) |
| 3 | GV_1 | 203 | 9 + 35 | 67.7 | TTT TTT TTT GGG CTT TGA TCC GAG GAT TTC CGA ATG GGG AGA CC | *Gardnerella vaginalis* (GV) |
| 4 | HSV1_2 | 23 | 9 + 35 | 71.0 | TTT TTT TTT TAC GTG GGT CAT TGG CGT GGG GGG TTA CAG CGA CA | *Herpes simplex virus-type1* (HSV1) |
| 5 | MG_2 | 173 | 9 + 35 | 61.2 | TTT TTT TTT GTT GAG AAA TAC CTT GAT GGT CAG CAA AAC TTT GC | *Mycoplasma genitalium* (MG) |
| 6 | MH_2 | 137 | 9 + 35 | 69.5 | TTT TTT TTT CGG GTC GAG AGA CTG AAC GGC CAC ATT GGG ACT GA | *Mycoplasma hominis* (MH) |
| 7 | NG_3 | 186 | 9 + 35 | 65.5 | TTT TTT TTT CGC CAA TAT ACC TAC CAA GCT CCA CTG ATA GGG CT | *Neisseria gonorrhea* (NG) |
| 8 | SA_3 | 89 | 9 + 35 | 58.9 | TTT TTT TTT ATC CTA AAA AAG GTG TAG AGA AAT ATG GTC CTG AA | *Staphylococcus aureus* (SA) |
| 9 | UU_0 | 725 | 9 + 35 | 61.6 | TTT TTT TTT TTA TGG ACG TCG TTT CGA TAT TCC ATC AGG TAC TG | *Ureaplasma urealyticum* (UU) |
| 10 | EF 913 | 752 | 9 + 35 | 60.7 | TTT TTT TTT TAT TAT GTT AGA TGG AAG TGG CTT AAG TCG CTG TG | *Enterococcus faecalis* (EF) |
| 11 | TV 913 | 31 | 9 + 35 | 64.1 | TTT TTT TTT GCT TCC GTA CAC TCA AGC TCA CAA CAC CAA CAT AC | *Trichomonas vaginalis* (TV) |
| 12 | KP 120_1 | 36 | 9 + 35 | 79.44 | TTT TTT TTT ATC TGG TGG ACT ACT CGC CGG TCA GCG AAA AAC AC | *Klebsiella pneumonia* (KP) |
| 13 | HSV2 913 | 57 | 9 + 35 | 71.6 | TTT TTT TTT GTC GCC GGG CAC CAC CAC GCC GTA TTG GTA TTC GT | *Herpes simplex virus-type2* (HSV2) |
| 14 | EC 913 | 383 | 9 + 35 | 60.3 | TTT TTT TTT GTA AAG TTA ATA CCT TTG CTC ATT GAC GTT ACC CG | *Escherichia coli* (EC) |
| 15 | IC_2 | 101 | 9 + 35 | 63.0 | TTT TTT TTT CTT TGT TCC CTA AGT CCA ACT ACT AAA CTG GGG GA | Internal control |
| 16 | PM | N/A | 15 + 22 | 59.0 | TTT TTT TTT TTT TTT TCA CGG TTA TCG CTG AAC TCG G | Position marker |

(*TM indicates the melting temperature of a probe without T-linker.)

According to another aspect of the present disclosure, there is provided a kit for diagnosis of genitourinary infection comprising the DNA chips for diagnosis of genitourinary infection according to any of the above-described embodiments; primer sets for amplifying DNA of genitourinary infection pathogens and beta-globin used as an internal control; and an anti-PM as an oligomer having a nucleotide sequence complementary to a position marker.

In an embodiment of the present disclosure, the primer set may be selected from the group consisting of a primer set for amplifying DNA of *Enterococcus faecalis* (EF) having for amplifying DNA of *Chlamydia trachomatis* (CT) having nucleotide sequences of SEQ ID Nos. 25 and 26, a primer set for amplifying DNA of beta-globin having nucleotide sequences of SEQ ID Nos. 27 and 28, a primer set for amplifying DNA of beta-globin having nucleotide sequences of SEQ ID Nos. 29 and 30, a primer set for amplifying DNA of *Escherichia coli* (EC) having nucleotide sequences of SEQ ID Nos. 31 and 32, a primer set for amplifying DNA of *Staphylococcus aureus* (SA) having nucleotide sequences of SEQ ID Nos. 33 and 34, a primer set for amplifying DNA of *Mycoplasma genitalium* (MG) having nucleotide sequences of SEQ ID Nos. 35 and 36, a primer set for amplifying DNA of *Herpes simplex virus*-type 1 (HSV1) having nucleotide sequences of SEQ ID Nos. 37 and 38, a primer set for amplifying DNA of *Herpes simplex virus*-type 1 (HSV1) having nucleotide sequences of SEQ ID Nos. 39 and 40, a primer set for amplifying DNA of *Trichomonas vaginalis* (TV) having nucleotide sequences of SEQ ID Nos. 41 and 42, a primer set for amplifying DNA of *Trichomonas vaginalis* (TV) having nucleotide sequences of SEQ ID Nos. 43 and 44, a primer set for amplifying DNA of *Neisseria gonorrhea* (NG) having nucleotide sequences of SEQ ID Nos. 45 and 46, a primer set for amplifying DNA of *Ureaplasma urealyticum* (UU) having nucleotide sequences of SEQ ID Nos. 47 and 48, a primer set for amplifying DNA of *Klebsiella pneumoniae* (KP) having nucleotide sequences of SEQ ID Nos. 49 and 50, a primer set for amplifying DNA of *Herpes simplex virus*-type 2 (HSV2) having nucleotide sequences of SEQ ID Nos. 51 and 52, and a primer set for amplifying DNA of *Herpes simplex virus*-type 2 (HSV2) having nucleotide sequences of SEQ ID Nos. 53 and 54.

In an embodiment of the present disclosure, the primer sets may further include a labeling element at a 5'-end thereof for detecting an amplified DNA complementarily bound to the DNA chip. The labeling element may be selected from the group consisting of Cy5, Cy3, FAM, TAMRA, Alexa Fluor, and Texas Red.

In an embodiment of the present disclosure, the genes of the target pathogens extracted from clinical samples of patients are divided into three groups and then amplified by multiplex PCR using gene-specific primer sets as shown in Table 3, followed by hybridizing the amplified products to the DNA chip according to the present disclosure, and fluorescent scanning to obtain a spot value (SV) and a signal-to-background ratio (SBR) from each spot on the DNA chip.

As used herein, the term 'SV (spot value)' refers to a difference in pixel intensity between a spot image and a background image of the spot. For example, when Cy3 is used as the labeling element, the SV value is equivalent to a value obtained by subtracting a background median pixel intensity at 532 nm from a spot) median pixel intensity at 532 nm and corresponds to 'F532median-B532median' in a microarray data file in GenePix Results (gpx) format. The term 'SBR (signal to background ratio)' refers to a ratio of a pixel value of a spot image to that of a background image surrounding the spot. When Cy3 is used as the labeling element, the SBR ratio is a ratio of a spot median pixel intensity at 532 nm to a background median pixel intensity at 532 nm, which may be calculated as a ratio of F532 median to B532 median by using the program, based on the F532 median and B532 median in the gpr file. When Cy5 is used as the labeling element, SV and SBR may be obtained by scanning at 635 nm, instead of 532 nm.

TABLE 3

Three groups of target genitourinary infection pathogens for multiplex PCR and nucleotide sequences of primers for DNA amplification

| Target | SEQ ID NO. | | Primer sequence (5'-3'☐) | Size | Grouping |
|---|---|---|---|---|---|
| EF | 17 | F | CCACAAGTACCATTCGTGCC | 509 | Group1 |
|  | 18 | R | CCAGGCATGGTGTTCAATTC |  |  |
| CA | 19 | F | TCA TTA CTG ATT TGC TTA ATT GCA C | 301 |  |
|  | 20 | R | AAC GTC CAC CAC GTA TAT CTT C |  |  |
| MH | 21 | F | CAATGGCTAATGCCGGATACGC | 334 |  |
|  | 22 | R | GGTACCGTCAGTCTGCAAT |  |  |
| GV | 23 | F | TATCAATTTCAACCGGCTCC | 275 |  |
|  | 24 | R | CCACAAAAACTGTGGTGTACC |  |  |
| CT | 25 | F | CTAGGCGTTTGTACTCCGTCA | 200 |  |
|  | 26 | R | TCCTCAGAAGTTTATGCACT |  |  |
| Beta-globin | 27 | F | CAGGCTGCCTATCAGAAAGT | 155 |  |
|  | 28 | R | GCTCAAGGCCCTTCATAATA |  |  |
| Beta-globin | 29 | F | TGG GTT AAG GCA ATA GCA A | 579 |  |
|  | 30 | R | TGT ATT TTC CCA AGG TTT GAA |  |  |
| EC | 31 | F | ATACCGCATAACGTCGCAAG | 554 | Group2 |
|  | 32 | R | CCACCGGTATTCCTCCAGAT |  |  |
| SA | 33 | F | CTCAGCAAATGCATCACAAA | 395 |  |
|  | 34 | R | CCAAGCCTTGACGAACTAAA |  |  |
| MG | 35 | F | AGTTGATGAAACCTTAACCCCTTGG | 281 |  |
|  | 36 | R | CCGTTGAGGGGTTTTCCATTTTTGC |  |  |
| HSV1 | 37 | F | TGGGACACATGCCTTCTTGG | 147 |  |
|  | 38 | R | ACCCTTAGTCAGACTCTGTTACTTACCC |  |  |
| HSV1 | 39 | F | ATC CTC GCT TTA GGA ACA ACT | 249 |  |
|  | 40 | R | CCA ACT GCC CCC TTA TCT A |  |  |
| TV | 41 | F | CATTGATAACGAAGCTCTTTACGAT | 112 |  |
|  | 42 | R | GCATGTTGTGCCGGACATAACCAT |  |  |

TABLE 3-continued

Three groups of target genitourinary infection pathogens for multiplex
PCR and nucleotide sequences of primers for DNA amplification

| Target | SEQ ID NO. | | Primer sequence (5'-3') | Size | Grouping |
|---|---|---|---|---|---|
| TV | 43 | F | TCT CCA AAG GTT TCT GAT ACA GT | 356 | |
|  | 44 | R | GTG AGC TCT GGG ACT GTA AGA | | |
| NG | 45 | F | GCTACGCATACCCGCGTTGC | 390 | Group3 |
|  | 46 | R | CGAAGACCTTCGAGCAGACA | | |
| UU | 47 | F | CAAGTTGGATCACATTTCCA | 210 | |
|  | 48 | R | GCCGTTTACACCTCAAACTT | | |
| KP | 49 | F | AAGATCCACTATCGCCAGCAGG | 231 | |
|  | 50 | R | ATTCAGTTCCGTTTCCCAGCGG | | |
| HSV2 | 51 | F | GGTTTGTTGTGAGGAGCCA | 114 | |
|  | 52 | R | CCTGGAAAATCTCCTTAGCC | | |
| HSV2 | 53 | F | CCA TGC ACG TAA AAC ACG | 345 | |
|  | 54 | R | GTG TGC CG TTT TTC GAG T | | |

In an embodiment of the present disclosure, each of the spots is determined to be positive or negative based on a cut-off value.

As used herein, the term 'cut-off value' refers to a reference value based on which it is determined whether each spot is positive or negative. Cut-off values for SV and SBR are applied to each spot. When a spot has an SV of 1000 or greater or an SBR of 2.5 or greater, the spot is determined to be positive. When a spot has an SV of less than 1000 or an SBR of less than 2.5, the spot is determined to be negative.

In an embodiment of the present disclosure, after determining whether each of the spots is positive or negative based on the above cut-off values, the number of positive or negative spots among the three replicate spots for each genitourinary infection pathogen may be counted to determine whether the sample is infected by the corresponding genitourinary infection pathogen.

For example, when the three replicate spots for each pathogen are all determined to be positive, the corresponding sample may be determined to be infected by the corresponding pathogen. When the three replicate spots for each pathogen are all determined to be negative, the corresponding sample may be determined not to be infected by the corresponding pathogen. When only one or two of the three replicate spots for each pathogen is determined to be positive, the overall test may be repeated with the corresponding sample to obtain accurate diagnosis results.

Thus, according to the embodiments of the present disclosure, the DNA chip for diagnosis of genitourinary infections including three replicate probe spots for each genitourinary infection pathogen may enhance sensitivity, specificity, and reproducibility of the diagnosis.

In an embodiment of the present disclosure, to determine the clinical effectiveness of a genitourinary infection pathogen detection method using the DNA chips according to any of the above-described embodiments, the accuracy of the detection method using the DNA chip was analyzed using 70 positive samples and 5 negative samples screened by PCR. The detection results were confirmed by sequencing. As a result, the DNA chip according to the present disclosure was found to have a sensitivity of about 95% and a specificity of about 100%, which are significantly higher than the PCR detection method with a sensitivity of about 50% and a specificity of about 80%. In addition, in comparative experiments using the probes according to embodiments of the present disclosure and widely-known probes, the probes according embodiment of the present disclosure were found to have higher sensitivities than the widely-known probes.

MODE OF THE INVENTION

One or more embodiments of the present invention will now be described in detail with reference to the following examples. However, these examples are only for illustrative purposes and are not intended to limit the scope of the one or more embodiments of the present invention.

Example 1

Preparation of New Probes With High Specificities to Genitourinary Infection Pathogens To develop new probes with high specificities to genitourinary infection pathogens, a target site of each of the genitourinary infection pathogens was selected as follows: First, a probe sequence was determined from pathogen specific sequences of 16S rRNA (18S rRNA for the eukaryote *Candida albicans* (CA)) and 23S rRNA genes that are widely used for phylogenetic analysis. When a suitable sequence was not available from these sequences, respective pathogen-specific genes were searched and selected as probe sequences, which are shown in Table 1 above along with GenBank Accession Nos. thereof. The nucleotide sequences of the target sites for respective pathogens and beta-globin gene, which were obtained using a BLAST engine (http://blast.ncbi.nlm.nih.gov) after the selection of the target sites, were cross-checked against the nucleotide sequences of primers designed by using Primer 3 (Whitehead Institute/MT Center for Genome Research). At least two candidate probes of 35 mer size that are able to minimize non-specific hybridization were designed for each of the pathogens by using OligoArray 2.0 (http://berry.engin.umich.edu/oligoarray).

Figure 1:
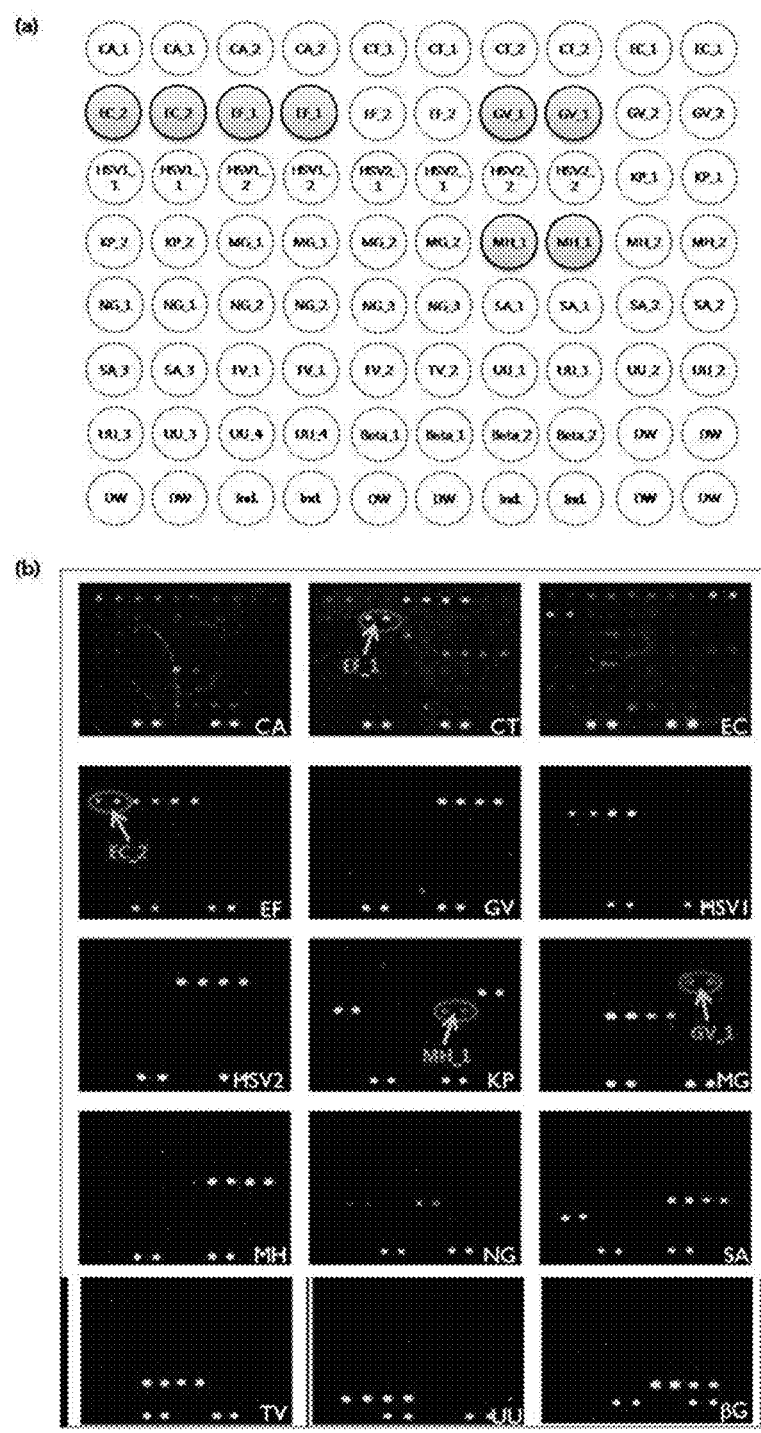
FIG. 1 is a schematic view (a) of a DNA chip for screening probes for detecting target pathogenic bacteria, according to an embodiment of the present disclosure, and a result (b) of fluorescent scanning of PCR products from the target pathogenic bacteria.

To verify the diagnostic capabilities of these candidate probes for the target pathogens, a screening test through hybridization using a DNA chip was conducted. As a result of the hybridization using a DNA chip designed as illustrated in FIG. 1 (*a*) to amplification products of respective pathogens, candidate probes EC_2, EF_1, GV_1, and MH_1 for EC, EF, GV, and MH of the fourteen pathogens were found to non-specifically hybridize to the amplification products of genes of irrelevant pathogens, as shown in FIG. 1 (*b*). These non-specifically hybridizing candidate probes were removed, and those candidate probes with relatively strong fluorescence intensities for the target pathogens, beta-globin, an internal control, and a position marker were selected as optimal probes, which are shown in Table 2 above along with nucleotide sequences thereof. Each of these probes has a linker consisting of nine Ts at the 5' end, followed by a 35-mer probe sequence specific to a STD pathogen. These T-linkers inserted as spacers may increase the hybridization efficiency between the probes and products from PCR.

Figure 2:
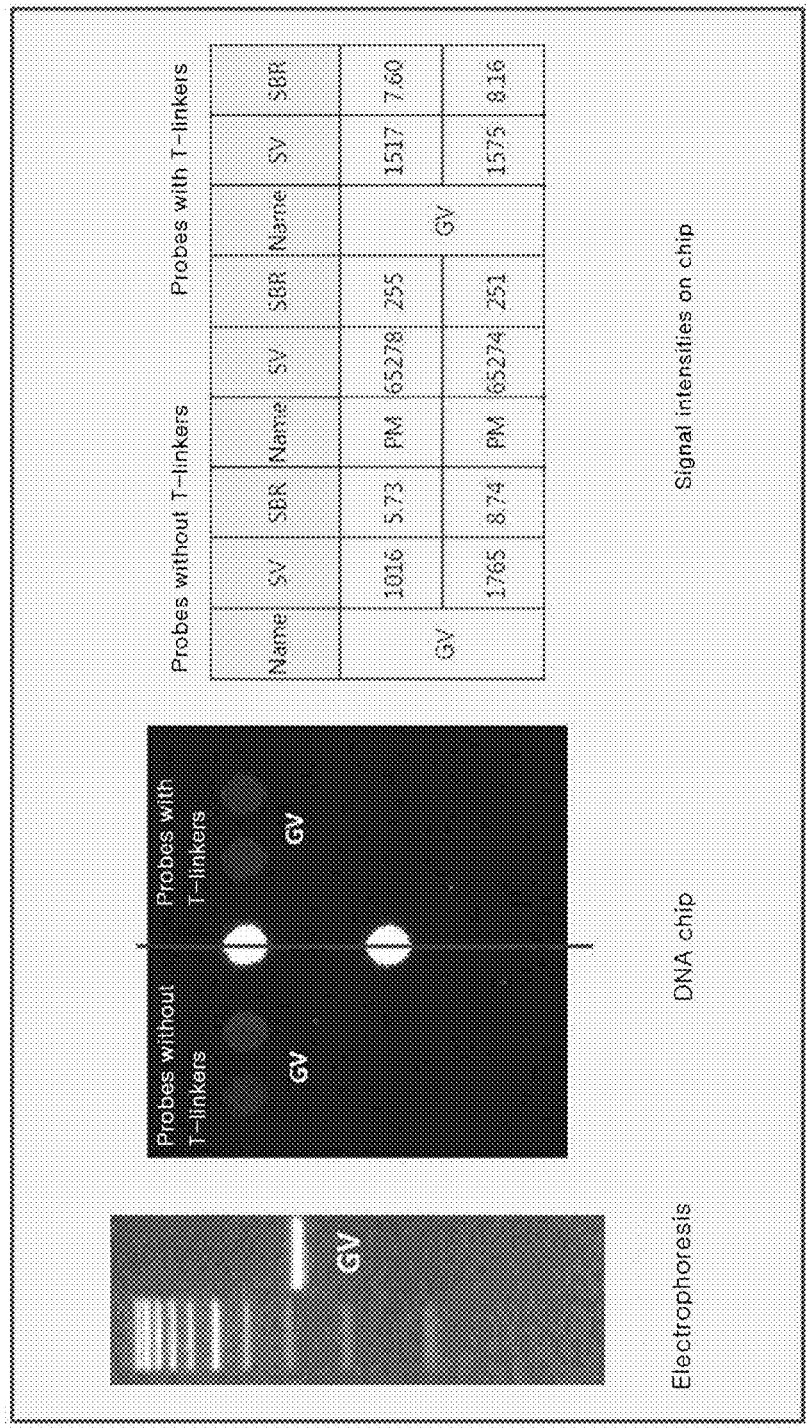
FIG. 2 shows that T-linkers enhance the stability of fluorescent signal intensities.

To identify hybridization efficiency depending on the presence or absence of T-linkers, after a GV single band was detected from a clinical sample with single GV infection by PCR detection, the clinical sample with single GV infection was subject to hybridization with DNA chips on which GV probes without a T-linker or GV probes with T-linkers were immobilized and the fluorescent signal intensities from the reaction of the DNA chips with the GV probes with or without T-linkers were determined. As a result, as shown in FIG. 2, the clinical samples with single GV injection were identified to be positive with both SV and SBR greater than the respective cut-off values thereof, irrespective of the presence or absence of T-linkers. However, for the probes without T-linkers, the signals from two replicate spots were 1016 and 1765, showing a large deviation and instability. For the probes with T-linkers, the fluorescent signal intensities from two replicate spots were 1517 and 1575, respectively, and thus found to be stably reproducible. Therefore, use of the probes with T-linkers was found to provide reproducible fluorescent signal intensities by increasing efficiency in a hybridization reaction, which indicates that the method of detecting a pathogen by using the DNA chip may reduce a test error when used in a clinical test based on a cut-off value.

DNA chip manufacturing, gene amplification, DNA chip hybridization, and hybridization detection were performed in the same manner as in Example 2 below. For amplification of the genes of the target pathogens, primers having nucleotide sequences as set forth in Table 3 above were used.

Example 2

Detection of Genitourinary Infection Pathogens by Using DNA Chip (1) DNA Chip Manufacturing To manufacture a DNA chip, an aldehyde-coated glass substrate was used as a slide for integrating probes. After removing dust from a surface of the glass substrate by using a high-pressure dust remover, the glass substrate was loaded onto a slide loading position of a microsputter. Then, SMP3 pins were washed with tertiary distilled water in an ultrasonicator and dried, and then installed into the pin installation site of the microsputter. With the pins for integration and the slide installed, the microsputter was operated at about 25° C. and a humidity of about 70%.

Figure 3:
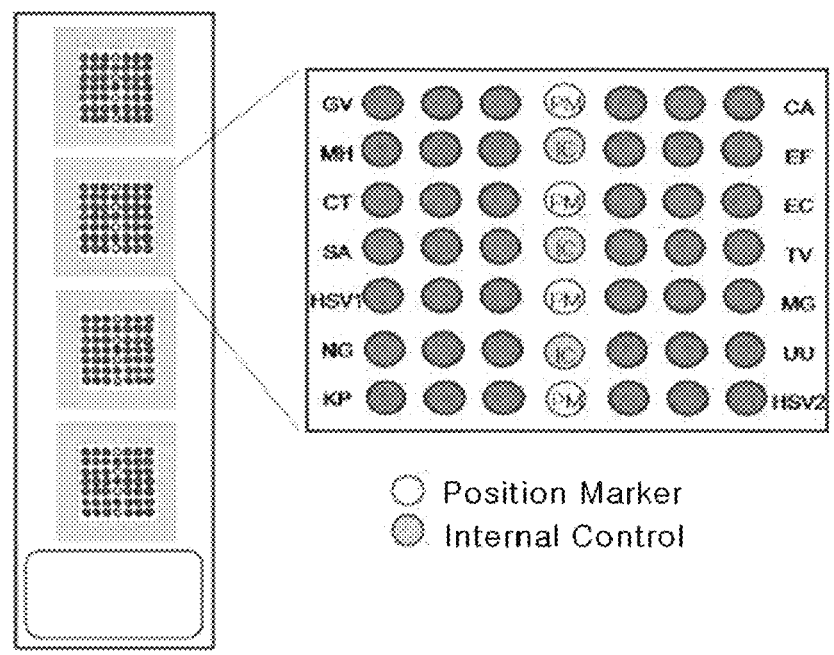
FIG. 3 is a schematic top view of a DNA chip according to an embodiment of the present disclosure and an immobilized pattern of probes on the DNA chip.

Each of the probes were prepared to be 25 pmol/µl in a 50% dimethyl sulfoxide (DMSO) solution, and stabilized at about −20° C. for about 16 hours or longer. The nucleotide sequences of the probes are shown in Table 2. Then, the microspotter was operated to immobilize the probes onto the aldehyde-coated glass substrate to allow the SMP3 pins to spot each probe three times as a 4-plex array, as illustrated in FIG. 3. A reaction chamber as reaction wells and a transparent film cover for preventing evaporation were assembled to the surface of the glass substrate with the immobilized probes.

(2) DNA Amplification

To amplify DNA of the target genitourinary infection pathogens, the target pathogens were divided into three groups for multiplex PCR. β-globin was used as an internal control. The nucleotide sequences of the forward (F) primers and reverse (R) primers used for amplifying beta-globin and DNA of the genitourinary infection pathogens, and sizes of amplification products thereof are shown in Table 3. To detect amplified DNA complementarily bound to the DNA chip manufactured as described above, a 5'-end of each reverse primer was labeled with Cy3.

Figure 4:
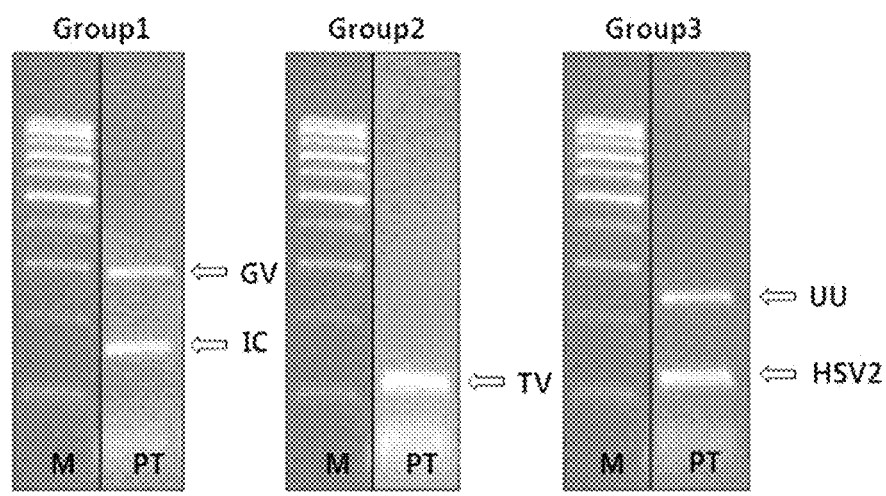
FIG. 4 illustrates the results of electrophoresis of PCR products from multiplex PCR of genes of pathogens extracted from patients with multiple infections by GV, UU, HSV2, and TV.

Multiplex PCR was performed on genes of the pathogens extracted from samples of patients with multiple infections by GV, UU, HSV2, and TV, under the same conditions as those for the DNA of the target pathogens. In particular, □ the genes of the pathogens extracted from each patient sample, 0.2 µM of a primer set, a 1×PCR reaction buffer (30 mM Tris-HCl, 30 mM KCl, 30 mM $(NH_4)_2SO_4$, 2 mM $MgCl_2$), 0.4 mM dNTPs, and 1.0 U i-star Taq polymerase (iNtRON Biotechnology, Korea) were mixed to prepare a reaction mixture, which was then subjected to DNA amplification using a Perkin-Elmer 9200 thermo-cycler (Perkin-Elmer, Norwalk, Conn.). The PCR conditions were as follows: heating for initial denaturation of double-stranded DNA at 94° C. for 5 minutes, 38 cycles of denaturation at 94° C. for 50 seconds, annealing at 57° C. for 45 seconds, and extension at 72° C. for 50 seconds, and then heating at 72° C. for 10 minutes for the final extension. The resulting PCR products were analyzed by agarose-gel electrophoresis to determine whether the PCR occurred or not, and sizes of the PCR products (refer to FIG. 4).

(3) DNA Chip Hybridization

To perform DNA chip hybridization reaction, a hybridization solution (5×SSC, 25% formamide, 25 ug/ml Human HybMasker Cot-1 DNA, 10% Dextran sulfate, and 0.1% SDS) stored in a −20° C. freezer was taken out of the freezer about 30 minutes prior to the hybridization reaction and pre-warmed in a 42° C.-reaction bath. Anti-PM (100 nM) stored in a −20° C. freezer was taken out of the freezer, thawed, and centrifuged at about 6000×g for about 10 seconds to collect a solution in a tube, which was then put into ice.

10 µl of the PCR amplification product from each sample group, i.e., a total of 30 µl of the amplification products from the three sample groups, were put into a microtube, mixed well by pipetting, and allowed to stand at 95° C. for 5 minutes. 40 µl of the pre-warmed hybridization solution was added into the microtube, and 1 µl of Anti-PM was added thereto using a pipette. Next, 70 µl of the resulting solution (71 µl) was slowly injected into an inlet in the film cover attached to the surface of the DNA chip, followed by assembly of the hybridization chamber. Any air bubbles in the space between the DNA chip and the reaction well (hybridization chamber) were removed by sweeping them out with a gloved hand if needed. After a hybridization reaction in a reaction bath at about 42° C. for about 2 hours, the hybridization chamber was removed from the reaction bath, and then disassembled to remove the DNA chip from the reaction chamber of the DNA chip and the transparent film cover.

A 50-ml tube for washing was filled with a washing solution 1 (2×SSC, 0.1% SDS) to a level at which the DNA chip was immersed, and the DNA chip was shaken up and down in the washing solution with a pincette about 10 to 15 times at a rate of 2 times a second. Then, the 50-mL tube containing the washing solution and the DNA chip was allowed to stand in a 50° C.-reaction chamber for about 5 minutes. Subsequently, another new 50-mL tube was filled with a washing solution 2 (0.1×SSC) to a level at which the DNA chip was immersed, and the DNA chip was shaken up and down in the washing solution with a pincette about 10 to 15 times at a rate of 2 times a second, and allowed to stand at room temperature for about 1 minute. The washing solution 2 was removed from the tube, and a new washing solution 2 was added thereto to repeat the washing of the DNA chip one more time.

The washed DNA chip was placed in a 50-mL dry tube, and was then centrifuged at 100×g for about 5 minutes to remove the moisture remaining on the washed DNA chip.

Figure 5:
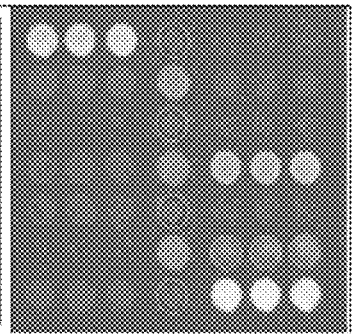
FIG. 5 is a fluorescent scan image of a DNA chip after hybridization.

Subsequently, the DNA chip was scanned with a fluorescent scanner GenePix 4000B (Axon Instruments, Union City, Calif.) (refer to FIG. 5), and the intensity of a signal from each spot on a scan image was analyzed to obtain an SV (spot value) and an SBR (signal to background ratio) for each spot.

The SV refers to a difference in pixel intensity between a spot image and a background image surrounding the spot, which is equivalent to a value obtained by subtracting a background median pixel intensity at 532 nm from a spot median pixel intensity at 532 nm, and which corresponds to 'F532median-B532median' in a microarray data file in a gpr format. The SBR refers to a pixel intensity ratio of a spot image to a background image surrounding the spot, a ratio of a spot median pixel intensity at 532 nm to a background median pixel intensity at 532 nm, which may be calculated as a ratio of F532 median to B532 median by using a program, based on the F532 median and B532 median in the gpr file.

(4) Determination of Results

To identify infection by genitourinary infection pathogens, it was determined whether each spot was positive or negative based on the following criteria (cut-off values):

Positive spot: a spot with an SV of 1000 or greater or an SBR of 2.5 or greater

Negative spot: a spot with an SV of less than 1000 or an SBR of less than 2.5

Upon determining whether each of the spots was positive or negative based on the above cut-off values, when the three replicate spots for each pathogen were all found to be positive, the sample was decided to have been infected by the corresponding pathogen. When the three replicate spots for each pathogen were all found to be negative, the sample was decided not to be infected by the corresponding pathogen. When only one or two of the three replicate spots for each pathogen was found to be positive, the test was decided to be insufficient for reliable decision and designated for retest.

As a result, the SVs and SBRs of the spots for each pathogen were obtained as shown in Table 4. The three spots for GV were found to have an SV of 1688, 1674, and 1763, and an SBR of 9.75, 9.81, and 10.23, respectively, and determined to be positive based on the above cut-off values. Consequently, a sample corresponding to the three spots was determined to be infected by GV. Likewise, the 13 remaining genitourinary infection pathogens were tested. As a result, infections by UU, HSV2, and TV were confirmed, while the other pathogens were not detected.

Figure 6:
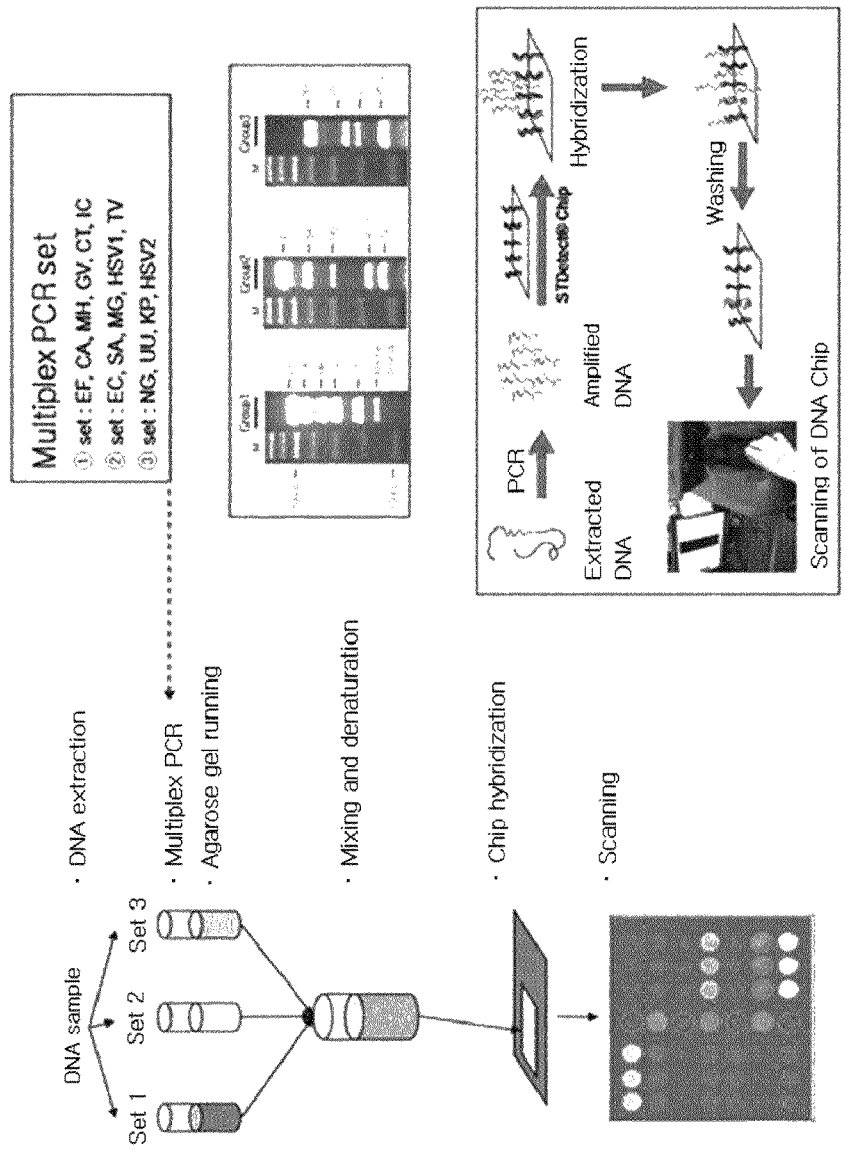
FIG. 6 is a schematic view of an overall assay process for detecting pathogens causing genitourinary infection, involving multiplex PCR, DNA chip hybridization, and fluorescent scanning.

The overall analysis process of the multiplex PCR, DNA chip hybridization, and fluorescent scanning as described above is schematically illustrated in FIG. 6.

TABLE 4

SVs and SBRs of spots after DNA chip hybridization reaction

|    | SV   | SBR   |    | SV  | SBR  |
|----|------|-------|----|-----|------|
| GV | 1688 | 9.75  | CA | 13  | 1.07 |
|    | 1674 | 9.81  |    | 24  | 1.12 |
|    | 1763 | 10.23 |    | 18  | 1.08 |
| MH | 105  | 1.55  | EF | 108 | 1.54 |
|    | 116  | 1.61  |    | 95  | 1.47 |
|    | 113  | 1.58  |    | 93  | 1.47 |

TABLE 4-continued

SVs and SBRs of spots after DNA chip hybridization reaction

|      | SV  | SBR  |      | SV    | SBR   |
|------|-----|------|------|-------|-------|
| CT   | 17  | 1.09 | EC   | 17    | 1.09  |
|      | 12  | 1.06 |      | 28    | 1.14  |
|      | 11  | 1.06 |      | 92    | 1.44  |
| SA   | 93  | 1.47 | TV   | 5820  | 30.39 |
|      | 107 | 1.54 |      | 5744  | 30.46 |
|      | 109 | 1.54 |      | 4599  | 24.46 |
| HSV1 | 86  | 1.43 | MG   | 23    | 1.12  |
|      | 108 | 1.52 |      | 29    | 1.15  |
|      | 97  | 1.46 |      | 35    | 1.18  |
| NG   | 18  | 1.09 | UU   | 10289 | 53.23 |
|      | 18  | 1.09 |      | 9116  | 47.51 |
|      | 17  | 1.09 |      | 8228  | 42.98 |
| KP   | 105 | 1.54 | HSV2 | 2520  | 14.13 |
|      | 111 | 1.57 |      | 2474  | 13.75 |
|      | 101 | 1.52 |      | 2205  | 12.25 |

Figure 7:
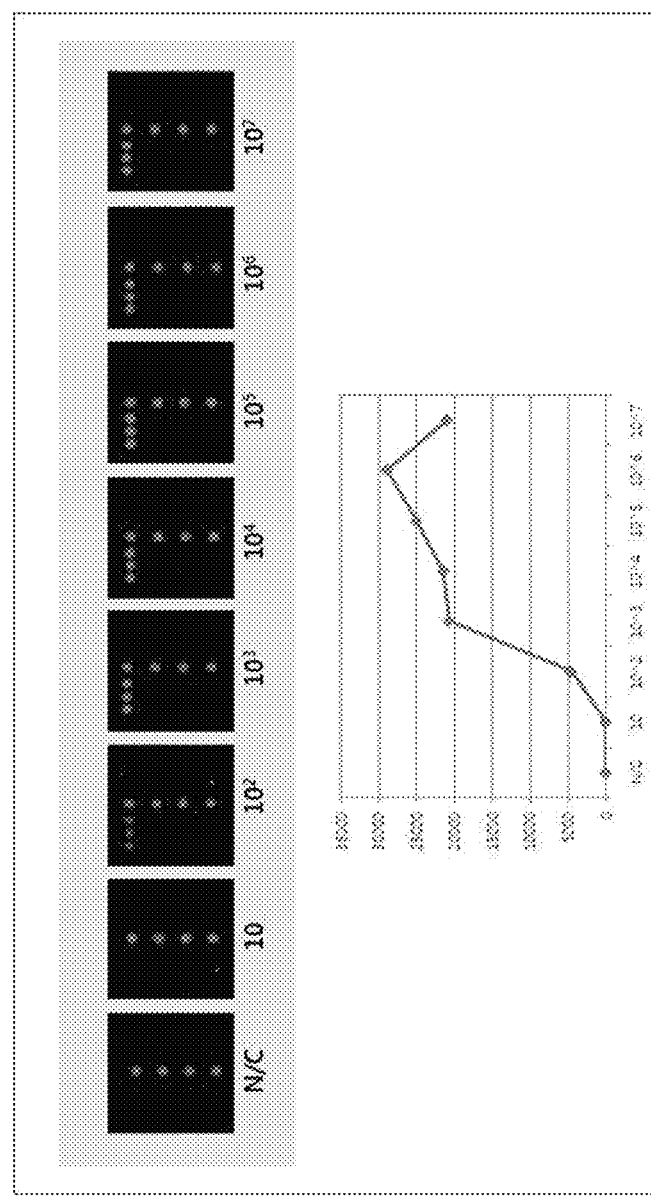
FIG. 7 is a fluorescent scan image of a GV reference in 0-$10^7$ copies, and a graph of SVs thereof for identifying a minimum detection limit.

To determine a detection limit in the method using the DNA chip according to an embodiment of the present disclosure, SV (spot value)s of the spots for GV were obtained in a range of $10^1$-$10^7$ copies. As a result, a minimum detection limit for GV was found to be $10^2$ copies, as shown in FIG. 7. The minimum detection limits for the 13 remaining pathogens were identified using respective clones of a target gene site thereof. As a result, all of the 13 pathogens were found to detectable with a minimum detection limit of about $10^2$ to $10^3$ copies.

Example 3

Sensitivity and Specificity of Detection Genitourinary Infection Pathogens by Using DNA Chip To determine the clinical effectiveness of the genitourinary infection pathogen detection method using the DNA chip according to an embodiment of the present disclosure, the accuracy of the detection using the DNA chip was analyzed using 70 positive samples and 5 negative samples screened by PCR, based on the sequencing thereof.

Figure 8:
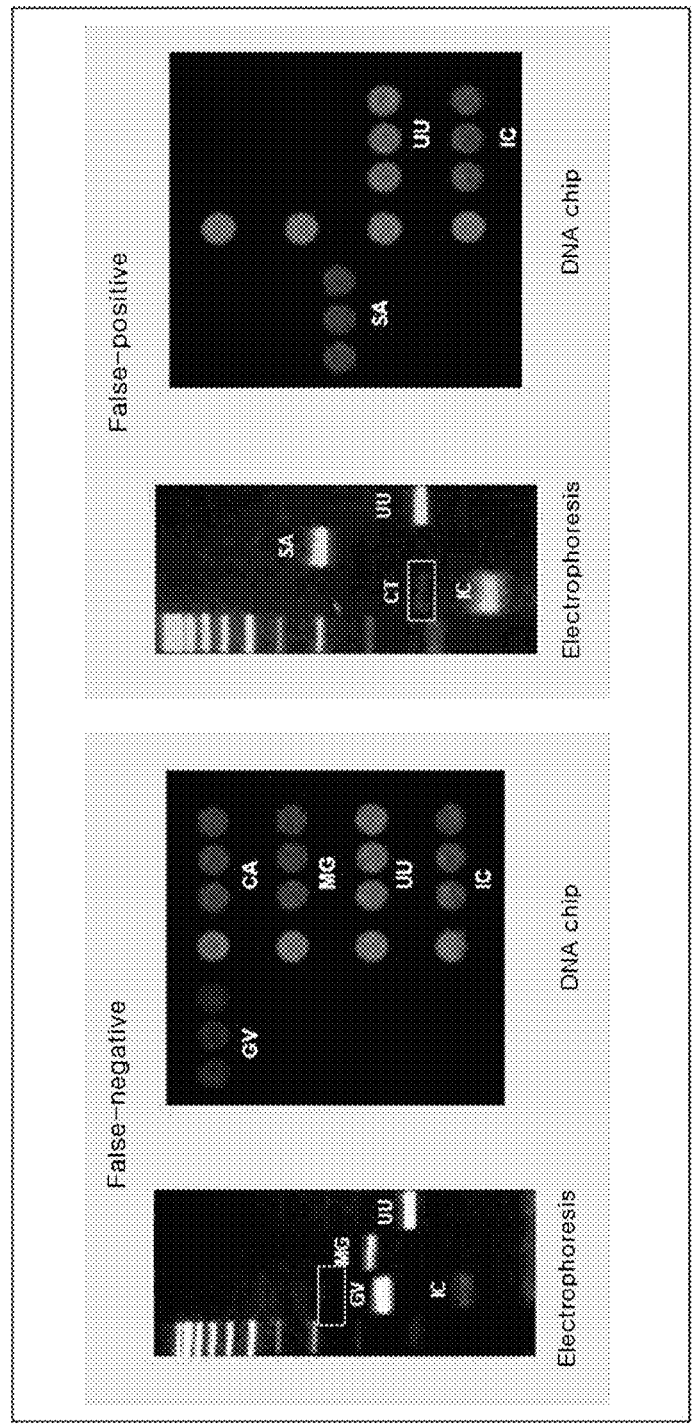
FIG. 8 illustrates the comparison of a PCR based detection and a detection using the DNA chip according to an embodiment of the present disclosure regarding sensitivity and specificity.

FIG. 8 shows the result obtained using clinical samples in an exemplary test for comparison of between PCR based detection and detection using the DNA chip according to an embodiment of the present disclosure. Referring to FIG. 8, among false negatives, GV, MG, UU, and IC were identified by agarose-gel electrophoresis in a PCR detection method, while CA, in addition to GA, MG, UU, and IC, was further identified by the detection method using the DNA chip. A difference in sensitivity between the two detection methods was confirmed by sequencing analysis. As a result, the clinical samples were found to include GV, MG, UU, IC, and CA, which indicates that the detection method using the DNA chip has a higher sensitivity than the PCR detection method, and may even be used to detect a trace amount of a pathogen.

In addition, among false positives, CT, SA, UU, and IC were identified by PCR detection, while SA, UU, and IC were identified by detection using the DNA chip. Upon verifying these results via sequencing analysis, CT identified by the PCR detection was determined to be false-negative. These results indicate that a tester may make a mistake of determining a false-positive non-specific PCR product to be positive in reading the result of the agarose-gel electrophoresis, and consequently, that the detection using the DNA chip has a higher specificity than the PCR detection method.

As a result of repeating these tests, using the DNA chip according to an embodiment of the present disclosure was found to have a sensitivity of about 95% and a specificity of about 100%, which are significantly higher than those of the PCR detection method with a sensitivity of about 50% and a specificity of about 80%.

TABLE 5

Nucleotide sequences of widely-known probes in use

| SEQ ID NO. | Probe name | Nucleotide sequence | Tm | % GC | Target pathogen |
|---|---|---|---|---|---|
| 55 | C_NG1 | gatattttc cgtaacgtct ctaagtct | 59.8 | 48 | Neisseria gonorrhea (NG) |
| 56 | C_NG2 | gtctctaagt ctgctttcgt ttgttg | 61.7 | 41.66 | Neisseria gonorrhea (NG) |
| 57 | C_CT1 | ttttcttcgt cagttaaacc ttccc | 59.9 | 40 | Chlamydia trachomatis (CT) |
| 58 | C_CT2 | gataggacat ggctctacaa cgaac | 59.8 | 40.9 | Chlamydia trachomatis (CT) |
| 59 | C_MH | atttgcaata ggaaatgatt gcaga | 59.8 | 32 | Mycoplasma hominis (MH) |
| 60 | C_MG | ccattactga cgcttaggct tga | 59.4 | 48 | Mycoplasma genitalium (MG) |
| 61 | C_CA | tgacaatggc ttaggtctaa ccaaa | 59.9 | 40 | Candida albicans (CA) |
| 62 | C_UU | gtgcaaatgt gatccaactt gg | 63.2 | 45 | Ureaplasma urealyticum (UU) |
| 63 | C_TV | gcaaaggcag tccttgacaa c | 60 | 52 | Trichomonas vaginalis (TV) |
| 64 | C_GV | aggctaaacc gagtacgtgt ga | 57.6 | 50 | Gardnerella vaginalis (GV) |

TABLE 5-continued

Nucleotide sequences of widely-known probes in use

| SEQ ID NO. | Probe name | Nucleotide sequence | Tm | % GC | Target pathogen |
|---|---|---|---|---|---|
| 65 | C_HSV1 | agggcggcga ctttgacga | 65.2 | 76 | Herpes simplex virus-type 1 (HSV1) |
| 66 | C_HSV2 | gggaggaagg cgcggagggg | 69 | 82 | Herpes simplex virus-type 2 (HSV2) |

To demonstrate that the new probes according to embodiments of the present disclosure have higher sensitivity and higher specificity than those of widely-known probes in use, DNA chips were manufactured using the new probes according to embodiments of the present disclosure and widely-known probes having nucleotide sequences in Table 5 above, disclosed in Korean Patent Application No. 10-2010-0058919, filed by GOODGENE INC., a diagnostic kit manufacturing company, in the same manner as in Example 2. In manufacturing the DNA chips, each of the known and new probes were spotted twice (refer to FIG. 9). The primers disclosed in Korean Patent Application No. 10-2010-0058919 were used as PCR primers for the known probes, and PCR was conducted using body labeling with Cy3-dCTP, under the conditions disclosed in Korean Patent Application No. 10-2010-0058919, followed by DNA chip hybridization and result determination in the same manner as in Example 2. A mixture of clinical samples identified as being infected by 12 species of pathogens by single PCR and sequencing was used as a sample.

Figure 9:
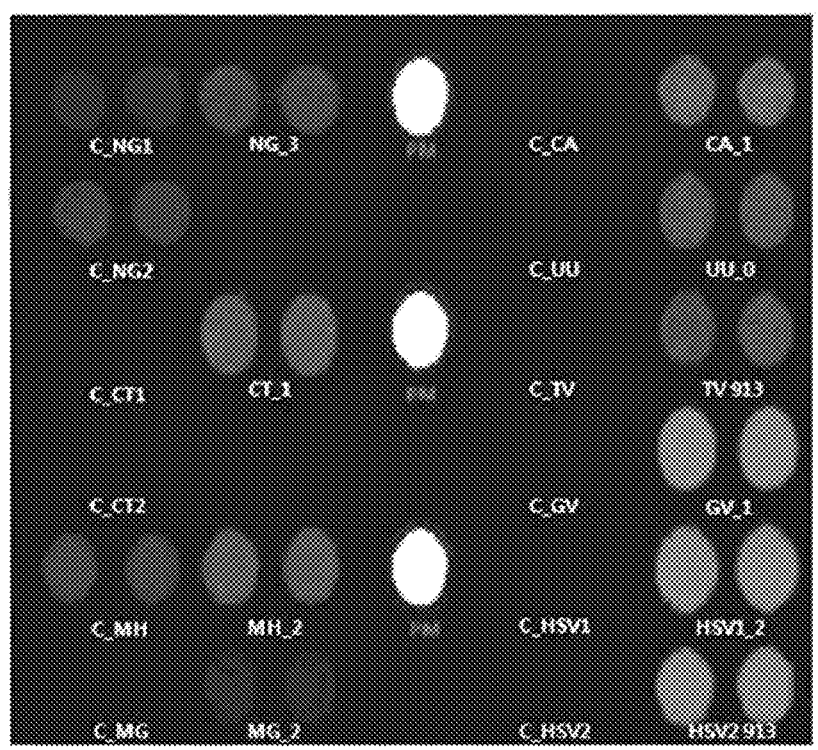
FIG. 9 illustrates the comparison of sensitivity between known probes and probes according to an embodiment of the present disclosure.

As a result, as shown in FIG. 9 and Table 6, fluorescent signal intensities from the known and new probes on the DNA chips were found to be significantly different. In most cases, the probes according to the present disclosure were determined to be positive spots, while the known probes were determined to be negative spots.

Table 6 shows the signal intensities from spots on DNA chip with the known and new probes. Referring to Table 6, the spots with the known probes for MH had an SV of 2417 and 2329, and an SBR of 7.71 and 7.73, respectively, while the spots with the new probes according to the present disclosure for MH had an SV of 4896 and 4634 and an SBR of 15.49 and 14.63. These values of the known and new probes were all above the cut-off values, and thus the spots with the known and new probes were both determined to be positive. However, the higher signal intensities from the new probes than those from the known probes indicate higher sensitivity of the new probes. The spots with the known probes for MG were determined to be negative with low signal intensities, while the spots with the new probes for MG were determined to be positive.

Through the above-described comparative experiments with the new probes and the known probes, the new probes according to embodiments of the present disclosure were found to have relatively high sensitivities.

INDUSTRIAL APPLICABILITY

As described above, a DNA chip for diagnosis of genitourinary infections according to the present disclosure may accurately and rapidly analyze genitourinary infections by

TABLE 6

Signal intensities from spots on DNA chip for genitourinary infection pathogens

| Name | SV | SBR | Name | SV | SBR | Name | SV | SBR |
|---|---|---|---|---|---|---|---|---|
| C_NG1 | 779 | 3.50 | PM | 65206 | 199.19 | C_CA | 1 | 1.00 |
|  | 754 | 2.86 |  |  |  |  | 17 | 1.06 |
| NG_3 | 2482 | 6.98 |  |  |  | CA_1 | 5681 | 20.26 |
|  | 2404 | 6.39 |  |  |  |  | 5918 | 21.20 |
| C_NG2 | 2024 | 8.20 |  | 0 | 1.00 | C_UU | 195 | 1.64 |
|  | 1923 | 7.59 |  |  |  |  | 199 | 1.68 |
|  | −5 | 0.98 |  |  |  | UU_0 | 3588 | 13.29 |
|  | −5 | 0.99 |  |  |  |  | 3810 | 13.70 |
| C_CT1 | 86 | 1.25 | PM | 65204 | 197.9909 | C_TV | 117 | 1.35 |
|  | 25 | 1.08 |  |  |  |  | 114 | 1.36 |
| CT_1 | 4849 | 15.78 |  |  |  | TV 913 | 3412 | 12.45 |
|  | 5120 | 16.24 |  |  |  |  | 3630 | 13.10 |
| C_CT2 | 15 | 1.04 |  | −14 | 0.957704 | C_GV | 8 | 1.02 |
|  | 26 | 1.08 |  |  |  |  | 24 | 1.07 |
|  | −5 | 0.98 |  |  |  | GV_1 | 20366 | 67.12 |
|  | 1 | 1.00 |  |  |  |  | 21555 | 72.14 |
| C_MH | 2417 | 7.71 | PM | 65192 | 191.0641 | C_HSV1 | 132 | 1.41 |
|  | 2329 | 7.73 |  |  |  |  | 25 | 1.08 |
| MH_2 | 4896 | 15.49 |  |  |  | HSV1_2 | 25053 | 81.04 |
|  | 4634 | 14.63 |  |  |  |  | 25703 | 85.55 |
| C_MG | 116 | 1.30 |  | 3 | 1.009494 | C_HSV2 | 138 | 1.46 |
|  | 42 | 1.12 |  |  |  |  | 152 | 1.52 |
| MG_2 | 547 | 2.64 |  |  |  | HSV2 913 | 22927 | 79.25 |
|  | 569 | 2.76 |  |  |  |  | 23008 | 78.73 | fourteen pathogens including multiple infections in various samples with high sensitivity, high specificity, and high reproducibility. Accordingly, the DNA chip may be advantageously used for diagnosis and treatment of genitourinary infections in primary health care institutions.

Although preferred embodiments of the disclosure have been described herein in detail, it will be understood by those skilled in the art that variations made thereto without departing from the scope of the disclosure or the appended claims.

The invention claimed is:

1. A DNA chip for diagnosis of genitourinary infection on which oligonucleotide probes consisting of SEQ ID NOs: 1-14 are immobilized, further comprising an internal control and a position marker, the position marker being an oligonucleotide consisting of SEQ ID NO:16.

2. The DNA chip of claim 1, wherein the internal control is an oligonucleotide probe consisting of SEQ ID NO:15.

3. The DNA chip of claim 1, wherein the DNA chip comprises at least one section with a collection of probe spots, the collection of probe spots comprising three replicate spots per oligonucleotide probe, and the section comprises replicate spots for the internal control and the position marker in the middle thereof.

4. A kit for diagnosis of genitourinary infection, the kit comprising:
the DNA chip of claim 1;
primer sets for amplifying DNA of genitourinary infection pathogens, and primer sets for amplifying beta-globin used as an internal control; and
an anti-position marker (PM) oligomer having a nucleotide sequence complementary to a position marker.

5. The kit of claim 4, wherein the primer sets are selected from the group consisting of a primer set for amplifying DNA of *Enterococcus faecalis* consisting of SEQ ID NOs:17 and 18, a primer set for amplifying DNA of *Candida albicans* consisting of SEQ ID NOs:19 and 20, a primer set for amplifying DNA of *Mycoplasma hominis* consisting of SEQ ID NOs:21 and 22, a primer set for amplifying DNA of *Gardnerella vaginalis* consisting of SEQ ID NOs:23 and 24, a primer set for amplifying DNA of *Chlamydia trachomatis* consisting of SEQ ID NOs:25 and 26, a primer set for amplifying DNA of beta-globin consisting of SEQ ID NOs: 27 and 28, a primer set for amplifying DNA of beta-globin consisting of SEQ ID NOs:29 and 30, a primer set for amplifying DNA of *Escherichia coli* consisting of SEQ ID NOs:31 and 32, a primer set for amplifying DNA of *Staphylococcus aureus* consisting of SEQ ID NOs:33 and 34, a primer set for amplifying DNA of *Mycoplasma genitalium* consisting of SEQ ID NOs:35 and 36, a primer set for amplifying DNA of *Herpes simplex* virus-type 1 consisting of SEQ ID NOs:37 and 38, a primer set for amplifying DNA of *Herpes simplex* virus-type 1 consisting of SEQ ID NOs: 39 and 40, a primer set for amplifying DNA of *Trichomonas vaginalis* consisting of SEQ ID NOs:41 and 42, a primer set for amplifying DNA of *Trichomonas vaginalis* consisting of SEQ ID NOs:43 and 44, a primer set for amplifying DNA of *Neisseria* gonorrhea consisting of SEQ ID NOs:45 and 46, a primer set for amplifying DNA of *Ureaplasma urealyticum* consisting of SEQ ID NOs:47 and 48, a primer set for amplifying DNA of *Klebsiella pneumoniae* consisting of SEQ ID NOs:49 and 50, a primer set for amplifying DNA of *Herpes simplex* virus-type 2 consisting of SEQ ID NOs: 51 and 52, and a primer set for amplifying DNA of *Herpes simplex* virus-type 2 consisting of SEQ ID NOs:53 and 54.

6. The kit of claim 4, wherein the primer sets further comprise a labeling element at a 5'-end thereof for detecting amplified DNA complementarily bound to the DNA chip.

7. The kit of claim 6, wherein the labeling element is selected from the group consisting of Cy5, Cy3, FAM, TAMRA, Alexa Fluor, and Texas Red.

8. A method for diagnosing genitourinary infection in a subject, the method comprising
(a) providing a DNA sample from the subject,
(b) applying the sample to a DNA chip on which oligonucleotide probes consisting of SEQ ID NOs:1-14 are immobilized, each nucleotide sequence immobilized forming a spot, wherein the DNA chip further comprises an internal control and a position marker, the position marker being an oligonucleotide consisting of SEQ ID NO:16,
(c) detecting signals from the spots on the DNA chip, and
(d) diagnosing genitourinary infection in the subject based on the intensity of signals.

9. The method of claim 8, wherein the genitourinary infection pathogen comprises *Escherichia coli, Klebsiella pneumoniae, Staphylococcus aureus, Enterococcus faecalis, Neisseria gonorrhea, Chlamydia trachomatis, Ureaplasma urealyticum, Mycoplasma hominis, Mycoplasma genitalium, Trichomonas vaginalis, Candida albicans, Gardnerella vaginalis, Herpes simplex* virus-type 1, and *Herpes simplex* virus-type 2.

10. The method of claim 8, wherein the internal control is an oligonucleotide probe consisting of SEQ ID NO:15.

11. The method of claim 8, wherein the DNA chip comprises at least one section with a collection of probe spots, the collection of probe spots comprising three replicate spots per oligonucleotide probe, and wherein the section comprises replicate spots for the internal control and the position marker in the middle thereof.

12. The method of claim 8, wherein step (a) comprises amplifying DNA in the sample with the primer sets are selected from the group consisting of a primer set for amplifying DNA of *Enterococcus faecalis* consisting of SEQ ID NOs:17 and 18, a primer set for amplifying DNA of *Candida albicans* consisting of SEQ ID NOs:19 and 20, a primer set for amplifying DNA of *Mycoplasma hominis* consisting of SEQ ID NOs:21 and 22, a primer set for amplifying DNA of *Gardnerella vaginalis* consisting of SEQ ID NOs:23 and 24, a primer set for amplifying DNA of *Chlamydia trachomatis* consisting of SEQ ID NOs:25 and 26, a primer set for amplifying DNA of beta-globin consisting of SEQ ID NOs:27 and 28, a primer set for amplifying DNA of beta-globin consisting of SEQ ID NOs:29 and 30, a primer set for amplifying DNA of *Escherichia coli* consisting of SEQ ID NOs:31 and 32, a primer set for amplifying DNA of *Staphylococcus aureus* consisting of SEQ ID NOs:33 and 34, a primer set for amplifying DNA of *Mycoplasma genitalium* consisting of SEQ ID NOs:35 and 36, a primer set for amplifying DNA of *Herpes simplex* virus-type 1 consisting of SEQ ID NOs:37 and 38, a primer set for amplifying DNA of *Herpes simplex* virus-type 1 consisting of SEQ ID NOs:39 and 40, a primer set for amplifying DNA of *Trichomonas vaginalis* consisting of SEQ ID NOs:41 and 42, a primer set for amplifying DNA of *Trichomonas vaginalis* consisting of SEQ ID NOs:43 and 44, a primer set for amplifying DNA of *Neisseria* gonorrhea consisting of SEQ ID NOs:45 and 46, a primer set for amplifying DNA of *Ureaplasma urealyticum* consisting of SEQ ID NOs:47 and 48, a primer set for amplifying DNA of *Klebsiella pneumoniae* consisting of SEQ ID NOs:49 and 50, a primer set for amplifying DNA of *Herpes simplex* virus-type 2 consisting of SEQ ID NOs:51 and 52, and a primer set for amplifying DNA of *Herpes simplex* virus-type 2 consisting of SEQ ID NOs:53 and 54.

13. The method of claim 12, wherein the primer sets further comprise a labeling element at a 5'-end thereof for detecting amplified DNA complementarily bound to the DNA chip.

14. The method of claim 13, wherein the labeling element is selected from the group consisting of Cy5, Cy3, FAM, TAMRA, Alexa Fluor, and Texas Red.

* * * * *